United States Patent [19]

Bhattacharjee

[11] Patent Number: 4,804,630
[45] Date of Patent: Feb. 14, 1989

[54] KIT AND METHOD FOR DETECTING LITHIUM IONS

[75] Inventor: Himangshu R. Bhattacharjee, Randolph, N.J.

[73] Assignee: Allied-Signal Inc., Morris Township, Morris County, N.J.

[21] Appl. No.: 25,542

[22] Filed: Mar. 13, 1987

[51] Int. Cl.$^4$ .................... G01N 21/78; G01N 33/20; G01N 33/52

[52] U.S. Cl. ........................................ 436/74; 422/56; 422/57; 422/61; 436/79; 436/164; 436/169

[58] Field of Search ............... 549/308, 309; 260/391; 422/55–58, 68, 61; 436/79, 63, 74, 164, 169

[56] References Cited

U.S. PATENT DOCUMENTS

| | | | |
|---|---|---|---|
| 4,407,960 | 10/1983 | Tratnyek | 436/2 X |
| 4,562,752 | 7/1985 | Perlman et al. | 422/56 |
| 4,670,385 | 6/1987 | Babb et al. | 436/135 X |
| 4,673,635 | 6/1987 | Yamanishi et al. | 436/135 X |

FOREIGN PATENT DOCUMENTS

| | | | |
|---|---|---|---|
| 0206316 | 12/1986 | European Pat. Off. | 435/28 |
| 0031641 | 3/1981 | Japan | 436/135 |

OTHER PUBLICATIONS

Hallas et al; Steric Effects in Di-and Tri-arylmethane Dyes, Part 13 CA87(4):24778g 1977.
Hawley; The Condensed Chemical Dictionary, 10th Edition, Van Nostrand Reinhold Co., New York 1981 p. 1080.
Hallas et al, J. Chem. Soc. Perkin Trans. 2, (4), pp. 450–456, 1977.
Handbook of Triarylmethane and Xanthrene Dyes, CRC Press, p. 297.
New York Times, Dec. 7, 1985, "Measuring Lithium in Body"–Stacy V. Jones.
Textbook Errors, 57 "The Oxygen Coordinates of Lithium"–G. Donnay and J. W. Gryder.
New Scientist Jul. 25, 1985 "Smuggling Lithium Across Membranes"–John Emsley.
Toxicology and Therapeutic Drug Monitoring (TDM), "Principles of Analysis and Current Usage"–Robert L. Murray.
Analytica Chimica Acta, 131 (1981) 117–122 "Improved Lithium Ion-Selective Electrode Based on a Lipophilic Diamide as Neutral Carrier"–A. Zhukov et al.
J. Am. Chem. Soc. 1985, 107, 4802–4803 "A Spherand Azophenol Dye: Lithium Ion Specific Coloration with Perfect Selectivity"–T. Kaneda et al.
Market Report, 45–48 "Psychotropic Research & Drugs".
Talanta, vol. 30, No. 4, pp. 275–276 "A Highly Sensitive Spectrophotometric Method for Determination of Micro Amounts of Arsenic"–W. Qian-Feng et al.
Chemistry Letters, pp. 1239–1240 (1985) "Highly Lithium-Selective Crown Ether Dyes for Extraction Photometry"–K. Kimura et al.
Lithium pp. 340–354 "The Unusual Character of Lithium Compounds"–W. Hart et al.
Ann. Rev. Med. 1982, 33:555–568 "The Role of the Lithium Ion in Medicine"–N. Rosenthal, M.D. et al.
Lithium, "Current Applications in Science, Medicine, and Technology"–R. Bach.
Studies in Physical and Theoretical Chemistry 27, "Ions and Molecules in Solution"–N. Tanaka et al.
Biochemical and Biophysical Research Comm., vol. 50, No. 2, 1973 "4,4'-Bis Diamethylaminodiphenylcarbinol . . . "B. Humphries et al.
Analytical Biochemistry 52, 127–142 (1973) "The Reaction of 4,4'-bis-Dimethylaminodiphenylcarbinol with the Sulfhydryl Group"–M. Rohrbach et al.

Primary Examiner—Michael S. Marcus
Assistant Examiner—Robert J. Hill, Jr.
Attorney, Agent, or Firm—Richard C. Stewart, II; Gerhard H. Fuchs

[57] ABSTRACT

A kit and method for detecting lithium ions in a sample. The kit includes a lithium ion selective color indicator which is a leuco precursor of an arylmethane dye dispersed in a matrix. In use, the color indicator is contacted with a sample and any color change therein is monitored. A color change in the indicator indicates the presence of lithium ions in the sample.

13 Claims, 1 Drawing Sheet

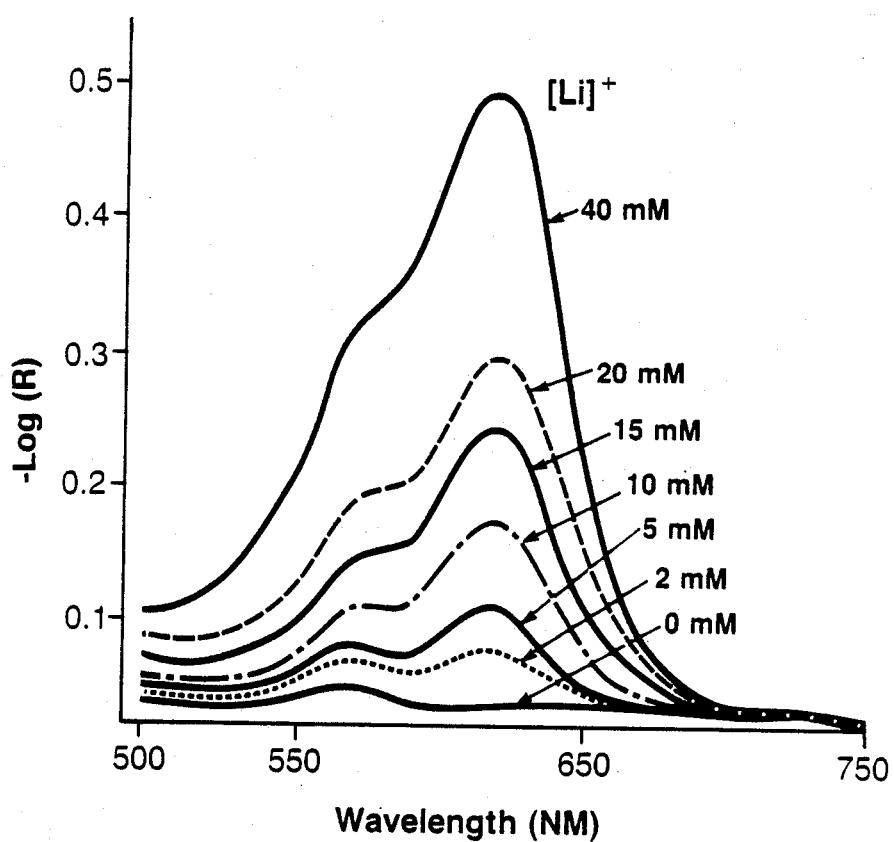

KIT AND METHOD FOR DETECTING LITHIUM IONS

FIELD OF THE INVENTION

This invention relates to a lithium selective color indicator which can signal the presence of lithium ions. In particular, this indicator may be used to identify lithium even in samples having a high content of other ions, such as sodium and potassium.

BACKGROUND OF THE INVENTION

Lithium has an important role in the management of a number of psychiatric disorders. Lithium is administered orally in the form of tablets, capsules, or liquid. Because lithium has the potential for having adverse effects on the kidneys and thyroid, it is important to carefully control the lithium dosage. Heretofore, the blood (serum) lithium level has been monitored through time-consuming and expensive procedures of flame photometry or atomic absorption spectrophotometry (See Toxicology and Therapeutic Drug Monitoring, Chap. 61, "Lithium" pp. 1377–1379.)

Alternatives to these methods of analysis are presently under investigation. Lithium ion-selective electrodes have been proposed to monitor whole blood during lithium therapy wherein a lipophilic diamide is utilized as a neutral carrier (Zhukor et al. "Analytica Chimica Acta,"131 (1981) 117–122). Macrocyclic polyethers have been used to extract various alkali metal ions, including lithium (K. Ueno and M. Takagi, "Studies in Physical and Theoretical Chemistry," Vol. 27, pp. 279–293 (1983)); and lithium ion-selective fluorescent emission with synthetic macrocyclic ligands, particularly crowned azophenols, is reported by Tanigawa et al. in Tetrahedron Letters, Vol. 25, No. 46, pp. 5327–5330 (1984).

U.S. Patent No. 4,556,068 describes a method for determining the amount of lithium in the brain and kidneys wherein a particular portion of the body is irradiated with neutrons, producing tritium atoms and hydrogen gas, which can then be measured from a patient's breath, indicating quantities of lithium in the part of the body examined.

However, what is needed in the art is an efficient, unobtrusive, highly selective mode of analysis for lithium content. Such a device and indicator system would aid the clinician in the rapid and inexpensive control of lithium dosage, to provide a dosage regime that is likely to be therapeutic without running the risk of toxicity. The present invention provides just such an indicator and analysis system through the use of a composition containing a precursor to an arylmethane dye. Arylmethane dyes have been known since the 1800's (see K. Venkatarman, The Chemistry of Synthetic Dyes, Vol. II, Academic Press, N.Y., 1952, pp. 705 ff.). However, uses of these dyes have typically centered around their colored nature and thus, the dye compounds have been used as coloring agents and colorants, biological stains and the like. By contrast, the colorless precursors of the dyes have not found such application. Humphries, et al. in Biochem. and Biophys. Res. Comm. 50, 2 (1973) report the use of 4,4'-Bis-dimethylaminophenylcarbinol as a reagent for sulfhydryl and cysteine residues. However, the species that interacts with these residues is not actually the precursor carbinol form of the compound, but rather the colored resonance forms of the compound. Thus, the carbinol form must be first converted to the resonance forms to interact with these residues.

BRIEF DESCRIPTION OF THE DRAWING

The FIGURE depicts the reflectance spectra of the areas of the indicator strips treated with serum solutions with and without lithium ions.

SUMMARY OF THE INVENTION

The present invention provides a lithium ion selective color indicator which comprises a leuco precursor of an arylmethane dye in a matrix, all or a portion of said indicator being capable of exhibiting a color when contacted with lithium.

Also provided is an analytical kit for the selective determination of lithium in a sample comprising:

(a) a lithium selective color indicator comprising a leuco precursor of an arylmethane dye dispersed in a matrix; all or a portion of said indicator adapted to exhibit a color when contacted with lithium, and (b) measuring means for measuring color development of the contacted portion of said indicator as an indication of lithium in the sample. Determination of the presence and/or concentration of lithium either by comparison to a standardized color intensity chart or by the measurement of a change in reflectivity can thus be made with the kit of the invention.

The analytical method of the invention is a method for the selective determination of lithium in a sample and comprises the steps of:

(a) contacting all or a portion of a leuco precursor of an arylmethane dye with said sample to effect a color change; and (b) monitoring the development of color as an indication of the presence of lithium in the sample.

DETAILED DESCRIPTION OF THE INVENTION

The present invention provides a lithium selective color indicator, analytical kit, and analytical methods for the selective determination of lithium in a sample. The lithium selective indicator of the invention comprises a leuco precursor of an arylmethane dye dispersed in a matrix, said composition capable of exhibiting color, which is detectable either visually or as a change in reflectivity, when contacted with lithium.

The types of leuco precursors useful in the invention may vary widely, the only requirement being that they be capable of exhibiting a detectable color when contacted with lithium.

Illustrative of the many leuco precursors useful in the present indicator are the leuco precursors of arylmethane dyes of the General Formula (I):

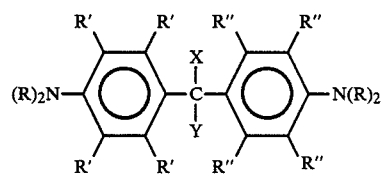

Wherein

X is H or OH and each R is independently H, (about $C_1$–$C_2$) alkyl, hydroxyalkyl, sulfonated alkyl, or a substituted phenyl group; each R' is independently H, about $C_1$-alkyl, or a sulfite group; each R" is independently H or about $C_1$-alkyl; and Y is H, alkyl, or

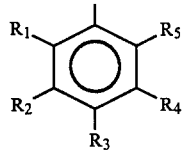

where $R_1$–$R_5$ are independently H, (about $C_1$–$C_4$) alkyl, halogen, sulfite, hydroxyl, or a substituted phenyl group.

Other leuco precursors useful in the indicator of the invention are those containing naphthalene or substituted naphthalenes, such as diphenylnaphthylmethane leuco bases. Some preferred leuco precursors are those what are capable of being transformed to dye forms upon contact with lithium, that visually exhibit vivid colors such as green, blue, or violet. Specifically, Malachite Green leuco precursors, Brilliant Green leuco precursors, and Crystal Violet leuco precursors are particularly preferred.

Most preferred are the colorless diarylmethane leuco bases or corresponding carbinols that exhibit a blue color upon contact with lithium, represented by the following general formula:

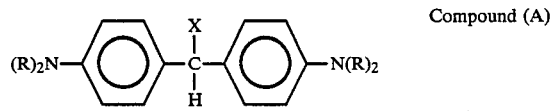

Compound (A)

where X is H or OH and (R) is about ($C_1$–$C_2$) alkyl.

Of these may be mentioned such compounds as 4,4'-bis-dialkylaminodiphenylmethane, such as 4,4'-bis-dimethylaminodiphenylmethane. Particularly preferred among these are the carbinol forms of the above such as 4,4'-bis-dialkylaminobenzhydrol, most preferred of which is 4,4'-bis-dimethylaminobenzhydrol, commonly known as Michler's Hydrol (Compound B). The carbinol forms are preferred in that they do not require an oxidizing step as described below prior to contact with sample for analysis of lithium. It is also particularly preferred that the starting compound be substantially colorless so as to minimize any background color.

It should be appreciated that one is not limited to the above-described colors for use as an indication of the presence of lithium. By selecting from among the above-mentioned leuco bases or their corresponding carbinols, as well as mixtures of two or more of any of them, a wide variety of desired colors can be obtained as an endpoint measure of the presence of lithium in a sample under analysis.

While the present inventor does not wish to be bound by any theory, it is believed that upon contact with lithium the leuco precursors are converted to arylmethane dyes and thus exhibit color. This can be illustrated as follows:

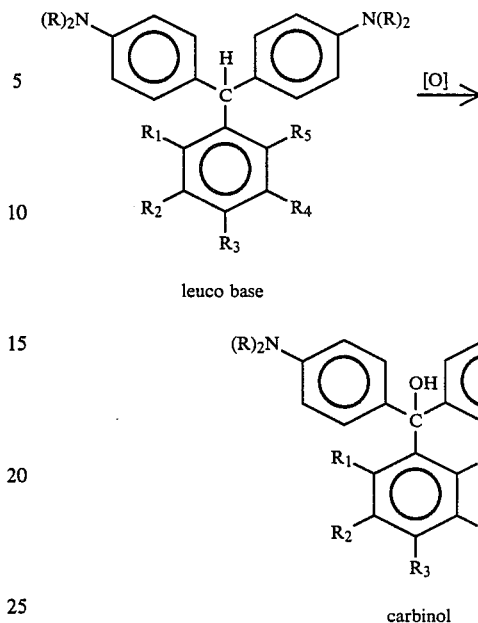

leuco base carbinol

Leuco precursors present in the base form are first converted to the carbinol form through oxidation. the requisite oxidation may be allowed to occur slowly upon prolonged contact with the open air. This process can also be expedited and enhanced by conventional techniques such as direct contact with an oxygen source in a laboratory hood or the like. Conventional chemical means of oxidizing may also be employed, such as dissolving the leuco base in ice-cold acids such as hydrochloric or acetic acids and the like, and then oxidizing with a calculated amount of freshly prepared lead peroxide, preferably in paste form.

The colorless carbinol form of the leuco precursor appears to be the precursor form that is capable of reacting with lithium to produce colored resonance structures, for example:

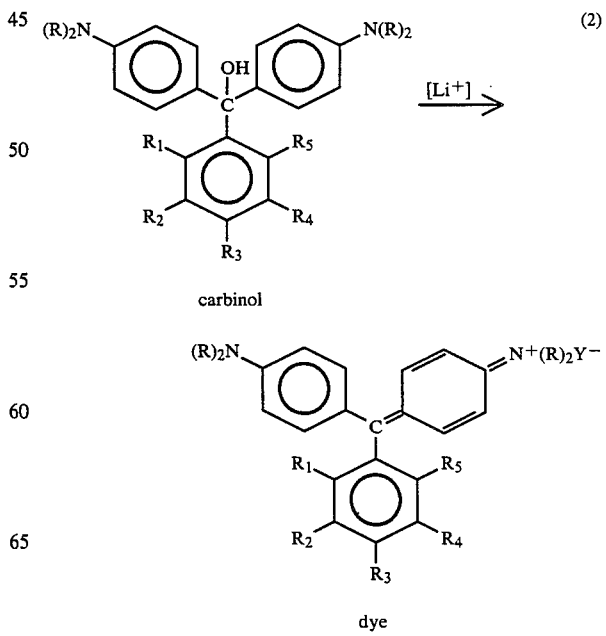

carbinol dye

-continued
and

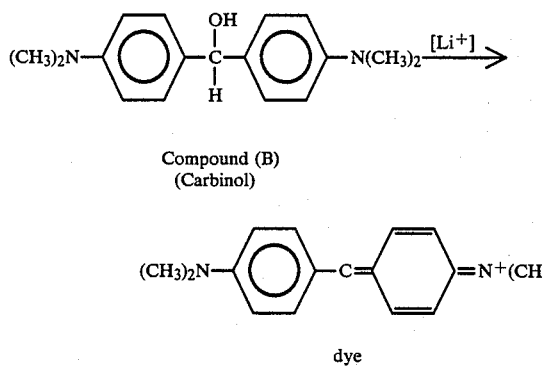

Compound (B)
(Carbinol)

$(CH_3)_2N-\bigcirc-C=\bigcirc=N^+(CH_3)_2$ dye

Wherein Li+ may be acting as a Lewis Acid to form LiOH.

The matrix component of the invention is any material that can serve to disperse the arylmethane dye precursor in a substantially homogeneous manner. This facilitates the oxidation step for those indicators requiring such a step, as well as provides a uniform surface for contact with a sample possibly containing lithium. The matrix component should be a solvent or dispersant medium that is appreciably inert, in that it is not inhibitory of desired color development. It is preferred that the leuco precursor be dispersed substantially homogeneously in this medium to achieve an even dispersion that provides a suitable surface area for contact with sample containing lithium, to enable the detectable development of color.

Materials useful as the matrix component vary widely and may be selected such as alcohols, aqueous alcohols and other organic solvents such as chloroform, acetone, and the like. The leuco precursor of the arylmethane dye can be dissolved directly into a solvent in the absence of any other dispersant and used in this liquid form as an indicator for the presence of lithium. Absolute ethanol is the preferred solvent in these cases, particularly a saturated solution of the precursor in the ethanol.

Other materials suitable as the dispersant medium include, polymeric binding materials, illustrative of which are polyvinylalcohol (PVA), polyvinylacetate (PVAc), polyethyelenes, polyamides, polypropylenes, polycarbonates, polystyrenes, poly(vinyl fluoride), poly(vinyl butyral), carboxylmethyl cellulose, ethylcellulose, ethylene-vinylacetate copolymers, cellulose propionate, polyacrylonitrile, poly(vinyl carbazole), polyacryl amide, poly(vinyl methyl ether), poly(vinyl methyl lactone), poly(vinyl pyrrolidone) and the like. It is preferable that the polymeric binding material be in combination with a compatible solvent, to produce a gel or gelatinous liquid. These types of materials are also readily available commercially. It is also within the contemplation of the present invention that any compatible combination or mixture of the above may be employed, especially a polymeric binder in combination with a suitable solvent system.

It is also preferred that the selected arylmethane precursor remain substantially colorless in its matrix to minimize background color interference. Further in this regard, although not critical, it is preferred to avoid acid-produced matrices, as color may tend to develop prematurely in even a slightly acidic environment.

A practical form of the indicator of the invention may be prepared from the leuco precursor and matrix by homogeneously suspending the leuco precursor of the arylmethane dye into the gel form of the polymeric binder material. The thus produced gelatinous liquid form of the indicator may be used to detect lithium.

As an alternative to the liquid form of the indicator of the invention, one may prepare the indicator in a solid form. The solid indicator generally comprises the leuco precursor dispersed in a polymeric matrix such as those described herein, to provide a reagent dispersion that is then coated onto a substrate. In these embodiments, the dispersion of the leuco precursor in the dispersant medium should be such that it lends itself to further coating onto a substrate. For this purpose, a homogeneous dispersion of fine particulate matter obtained by mechanically blending the mixture is generally preferred.

The size, shape, and thickness of the substrate employed varies according to intended use. In some embodiments, the substrate can be in the form of strips, providing an indicator that may be dipped into a sample under analysis, or onto which a sample under analysis may be conveniently deposited. Any suitable substrate may be used, including paper, filter paper, cardboard, metal, thermoplastics, nonabsorbing plastic materials, and the like. To minimize the incidence of background color, it is particularly preferred to utilize nonabsorbant plastic as the substrate such as polymers formed from $\alpha$, $\beta$ unsaturated monomers. Illustrative of these are polyesters, polyethylenes, silicones, polyethylenes coated with silicone, polytetrafluoroethylenes and the like. Particularly preferred for characteristics such as resistance to heat and also a white background that enhances the color development of the arylmethane precursors are the polytetrafluoroethylenes and polyethylene films coated with silicone.

Any suitable method may be used to apply the reagent dispersion to the substrate, including spraying with an airbrush, silk-screening, coating with a doctor's blade or Mayer rod or similar techniques conventionally used in the printing industry. Depending on the method used, it may be necessary to control the viscosity of the solution by for example, choosing a polymer with a relatively lower molecular weight to serve as the dispersing medium.

After coating the dispersion onto the substrate, the coated material is dried by conventional techniques such as hood drying, oven drying, ambient temperatures, and the like to produce a film that adheres to the substrate. Temperatures of below about 75° C. may generally be employed in oven drying as long as the chosen substrate or indicator matrix does not soften appreciably under these conditions.

Coating thickness of the reagent film on the substrate may be optimized to facilitate obtaining efficient and reproducible results upon contact with lithium. Preferred coating thicknesses generally range from about 25 microns to about 250 microns, with 50 microns to about 100 microns particularly preferred. Multiple coatings may also be employed to obtain desired thicknesses.

In the analytical method of the invention, a sample under analysis for lithium content is contacted with a leuco precursor of an arylmethane dye by any convenient method, preferably utilizing one of the above-described forms of the present indicator.

The sample under analysis, possibly containing lithium, may be present as a crystalline solid, or may be dissolved or dispersed in one or more various solvents including water. Alternatively, the sample may be in the form of a biological, physiological, environmental specimen or the like, in which case any lithium that might be present could be in a substantially aqueous environment. Other ions may be present in amounts that may vary widely, and surprisingly, these ions are not expected to interfere with the detection of lithium to any appreciable extent. Background color may develop, however, depending on the type and amount of interfering components that also present in the sample. Those of skill in the art should appreciate that appropriate control measures may be employed to account for any background levels.

The present method is particularly suited for the analysis of biological specimens, such as for example, blood serum, for the detection of lithium used for medical treatment even in the presence of substantial amounts of naturally occurring $Na^+$ and $K^+$ ions. Lithium has a relatively narrow therapeutic range. Doses of 0.9–2.0 meq/L can alleviate acute manic symptoms in some cases, while doses of about 2.0 meq/L or above can produce poisoning. The sensitivity of the present indicator is within this critical range. In general, concentrations as low as 0.9 mM may be detected. However, one of skill in the art will appreciate that conventional sample clean-up techniques will aid in attaining sensitivity in this range. For example, in the preferred forms of analysis of blood samples, the samples are first treated to produce blood serum. This may be accomplished by conventional techniques for removal of red blood cells. This pretreatment is to ensure that developing color can become conspicuous, and not be masked by the red blood cells. Removal of other ions and the like by conventional techniques may also be desirable.

In some preferred embodiments, a liquid indicator is contained in a glass or other suitable vesicle. Alternatively, a portion of the liquid indicator is spread onto a glass slide and allowed to dry under heating of about 80° C. A small amount of sample in liquid form, possibly containing lithium, is deposited either into the container or onto the center of the slide and a visual observation of color development is made. Color development is often in the form of a circle or ring surrounding the deposited sample, and the color may be expected to vary in intensity relative to the amount of lithium present in the sample. The colored area may be monitored visually or by reflection measurements using conventional equipment and technique.

In more preferred forms, a test strip or disk or the like prepared by coating a suitable substrate as described herein is used in place of the liquid indicator. The solid indicator is dipped into a liquid sample under analysis, or a drop of sample is placed onto it. Various concentrations of sample under analysis may be tested and the development of color hue may be visually compared against that produced by known concentration of lithium. Alternatively, the presence of lithium may be detected by a change in reflectivity utilizing conventional analytical devices for this purpose, such as those described for a reflectance spectrum. Suitable wavelengths should range from about 450 nM to about 750 nM. The peak for the dye form of the preferred compounds is expected to be about 615 nM notwithstanding shifting of the spectra due to other components in the sample. For greater detail on reflectance measurements, see "Color in Business, Science and Industry," Deane Judd and Gunter Wyszecki, John Wiley & Sons, New York.

No matter which form of the indicator is utilized, liquid or solid, an optional heating or drying step is preferably employed after contact with sample containing lithium, to hasten the development of color. Heat may be applied by any convenient means such as a hot plate, infrared heater and the like. It is preferred that the heat be applied evenly over the area where the sample has contacted the indicator. Temperature ranges of about 60° C. to about 90° C. are generally useful, with about 75° C. to about 80° C. particularly preferred. The length of time heat is applied to the indicator varies widely but should not be so long as to soften the substrate, which will in turn affect the color aesthetics. About 2 minutes to about 10 minutes of heating is preferred in most practical applications depending on the amount of reagents contained in the indicator to be dried.

In the analytical kit of the present invention, the preferred form of the reagent comprises a leuco precursor, particularly 4,4'-bis-dimethylaminobenzhydrol (Compound B) and derivatives thereof, dispersed in a polymer binder and coated onto polyethylene film coated with silicone. The resulting reagent film can be provided as strips that can vary widely in size and shape. Optionally, a protective covering may be provided on top of each of the strips, to protect the coated surface until use. Conventional coverings may be employed for this purpose such as polyester, polyethylene and the like, and most be removed either physically or chemically prior to use of the indicator strips.

It is within the contemplation of one embodiment of the invention that a predetermined standardized color intensity chart be used in conjunction with the reagent strips for visual determination of concentrations of lithium in samples. In some preferred embodiments, the analytical kit provides a liquid indicator system or solid indicator wherein at least a portion of the indicator will change from a colorless or white background color to a visually detectable blue color, often a dark blue, in a relatively short period of time. In some embodiments, color can be expected to develop in a matter of minutes after contact with lithium depending on the sample that is assayed. This color development may then be compared against the standard color development of known concentrations of lithium.

In the more preferred embodiments, it is contemplated that a scanning light source with appropriate wavelengths will be used to measure change in reflectivity as a highly sensitive indication of the presence and/or concentration of lithium. As but one example of this are situations involving the analysis of biological specimens, wherein a bar code system may be conventionally utilized. For example, certain data pertaining to a particular patient may be coded onto a bar code, such as those conventionally used for marking products in a supermarket or the like. A portion of the bar code would also contain the indicator of the invention. In this manner, a patient's lithium content in various body fluids, and particularly blood, may be tested routinely in a very efficient, quick, and inexpensive manner. The entire bar code may be disposable, or simply the portion of the code that contains the lithium indicator.

It should be appreciated that the indicators, kit and method of the invention may be used to selectively determine the presence and/or concentration of lithium in a variety of samples other than body fluids, including but not limited to environmental, physiological, biological and the like. The following examples are illustrative of compositions falling within the scope of this invention. They are, of course, not to be considered in anyway limitative of the invention since numerous changes can be made with respect to selection of leuco precursors, solvents, coatings, ranges of proportions, and the like.

EXAMPLES

Example 1

On a piece of filter paper, equal amounts of Compound B and lithium salts (either LiCl or LiNO$_3$) were mixed and held together. Within 10 minutes, blue color started to develop and gradually intensified to deep blue and eventually to violet. Similar experiments were performed by replacing the lithium salt with corresponding sodium and potassium salts. Only a faint blue coloration appeared after a period of twenty-four hours with either the sodium or potassium salts.

Example 2

Using a mortar and pestle, equal amounts of lithium, sodium and potassium chlorides were ground together (mixture 1). Similarly, another mixture (mixture 2) was prepared which contained only sodium and potassium chlorides. By carrying out the mixing reactions with the dye precursor similar to Example 1, it was discovered that color development occurred only with the mixture 1.

Example 3

Thirty (30) mg of Compound B was placed on a glass slide. The solid sample was partially soaked by adding a drop of methanol. On top of this suspension was added 30 mg of lithium chloride. Intense blue coloration was instantly developed (eventually turned to violet). The above procedure was then repeated separately with sodium and/or potassium chlorides. Only a faint blue color developed after several hours in the latter cases.

Example 4

Example 3 was repeated using a drop of water instead of methanol. A light blue coloration appeared in two hours when lithium chloride was added, whereas the mixture remained colorless when sodium chloride or potassium chloride was added.

Example 5

Example 3 was repeated using various other organic solvents such as ethanol, chloroform, and toluene instead of methanol. Lithium chloride produced the same intense coloration in ethanol similar to the coloration produced when it was in methanol. However, in chloroform, the coloration was much less intense. In toluene, only a light violet color developed after five minutes. Sodium and potassium salts again did not produce any noticeable coloration in either solvent.

Example 6

Example 3 was repeated by adding a drop of 1% lithium chloride solution in water in place of the solid salt. Initial color development was rather sluggish and after 2 hours, the color intensified to moderately violet. No color was developed by using aqueous solutions (1% each) of either sodium chloride or potassium chloride.

Example 7

Example 3 was repeated using a mixture of solvents such as alcohol and water in 50:50 proportion instead of methanol alone. Developed color with lithium salts was rather comparable with either methanol or ethanol alone.

Example 8

An aqueous medium (gel) was prepared by placing 4 g of a polyvinyl alcohol (PVA) in 100 mL water and heating the mixture at 80° C. for 30 minutes. The PVA used was obtained from Aldrich and had a M.W. of 115,000. It was 99–100% hydrolyzed. Into 1 mL of the PVA gel was placed 20 mg of Compound B. A good mixture was obtained by grinding. Strips of filter paper ($\frac{1}{2}"\times 4"$) were coated with the above mix either by using a Mayer rod or through a silk screen. The coated strips were then dried at room temperature inside a hood for one hour. Dried samples were white in appearance. The strips were cut out in $\frac{1}{4}"\times\frac{1}{4}"$ pieces for using in the individual tests and they were stored in the dark at room temperature.

In another set of experiments, aqueous solutions of lithium, sodium and potassium nitrates were prepared. The concentration of the solutions were varied from 20 mM to 100 mM. Individual coated pieces were soaked separately with 100 mM solutions of LiNo$_3$, NaNO$_3$, and KNO$_3$ and placed separately on top of glass slides. Upon heating the glass slides for 2 minutes at 80° C., a vivid blue color developed on strips impregnated with LiNO$_3$ solution. The other strips developed some coloration, which was however, easily distinguished from that produced by the lithium contact.

Example 9

Example 8 was repeated by using substrates other than filter paper. It was discovered that the background color can be substantially minimized by coating nonabsorbing plastic substrates. Thus, polyester strips (obtained from Kapak Corp., Minnesota) coated with the leuco base materials were found to develop color rather exclusively with Li$^+$ ion. In an actual experiment, coated strips of polyester were placed on a hot plate set at 80° C. Over the coated area was added a drop of an aqueous solution of LiNO$_3$. Blue color developed as soon as water evaporated, within 7–10 minutes. Identical experiments done with K$^+$ and Na$^+$ solutions did not leave any noticeable color on the coated strips. Color development was observed with various concentrations of LiNO$_3$ solutions varying from 20 mM to 100 mM. The time required for color development, as well as the intensity of color, varied according to the concentrations of LiNO$_3$ solutions employed.

Example 10

Example 8 was repeated with other plastic substrates. Films were received from the "Custom Coating and Lamination Corporation" (polyethylene coated with silicone). It was determined in this experiment that a transparent film which can withstand a temperature of around 100° C. (without softening) is preferable. Also, once coated, the film should remain completely colorless during the process of heating, in order to provide a sharp contrast when intended color is developed by the addition of lithium, particularly an aqueous solution.

Initially, the mixture of carbinol and polyvinyl alcohol gel were finely grounded i a Waring blender. To gain uniformity in coatings, the mixture was then sprayed through the nozzle of a paasche airbrush. Repeating the procedure described in Example 9, it was discovered that the above coated film can become useful in exclusively identifying aqueous solutions containing lithium ions.

To identify the lower limits of $Li^+$ *concentration, solutions differing in concentration of lithium ions from* 100 mM to 2 mM were tested. In each case, after evaporation of water, a blue-colored ring developed. As expected, the intensity of color varied according to the concentrations of $Li^+$ ions employed. Identical experiments, when performed separately using 100 mM solutions of $K^+$ and $Na^+$ ions, did not develop any such colored rings. A similar negative result was also observed when the coated surface was treated with deionized water alone. The system identified the $Li^+$ ions at very low concentrations and in the presence of excess $Na^+$ and $K^+$ ions.

Example 11

Presence of $Li^+$ can also be determined with the solution form of indicator. A concentrated solution of Compound B was initially prepared in absolute ethanol (USI brand). The carbinol remains colorless in absolute ethanol. A piece of polyethylene film used in Example 10 was placed on a hot plate (set at 80° C.). On top of the film was added a drop of an aqueous solution of $LiNO_3$ (20 mM). After 6 minutes, was added 2 drops of the alcoholic solution of the carbinol on top of the $LI^+$ drop. After a few minutes, a substantial blue color developed. Blue-colored rings appeared even when low concentration of lithium ion (such as 2 mM) were employed. Only a faint blue coloration eventually developed when identical experiments were carried out using even as high as 100 mM aqueous solutions of either $Na^+$ or $K^+$ ions.

In a similar experiment, one drop of $Li^+$ solution was first mixed with 3 drops of the alcoholic solution of the carbinol. One drop of the above mixture was placed on a polyethylene sheet held on top of a hot plate (set at 80° C.). A blue colored ring developed as soon as the alcohol and water evaporated.

Example 12 TESTING PRESENCE OF $Li^+$ Ions in Blood Serum

Two varieties of serum samples were tested. While the fetal bovine serum (Hyclone Laboratories, Inc.) did not have any lithium ions, the control human serum (Fisher Scientific) contained 0.5 mM of $Li^+$. Both of them had the usual amounts of alkali and alkaline earth metal ions which ranged from: $Na^+$: 138–145 mM, $K^+$: 4–20 mM, $Ca^{++}$: 10–13 mM; and $Mg^{++}$: 2–27 mM.

Various amounts of solid lithium salts ($Li^+$ content varying from 2–100 mM) were separately added to each of the above serum solutions to distinguish the extent of color development between lithium-free and lithium-containing serum samples. One of the experiments involved treating such solutions with a concentrated solution of the carbinol (as prepared in Example 10) and placing a drop of the mixed solution on a plastic film (as described in Example 11). Upon drying each mixed solution, it was observed that lithium-containing solutions (even having low concentrations of lithium) developed distinctly visible blue coloration. The lithium-free soltuions, on the other hand, developed only feeble blue color.

One advantage of treating the serum with an alcoholic soltuion of the carbinol is that the serum solution gets dispersed on the surface of the film, thus loosing its intense yellow coloration. The yellow coloration can mask the less intense blue color that develops with the addition of the reagent. Even with solutions having low lithium content, it is thus relatively easy to visualize the developed color with this dispersion. Good reproducibility of results can be expected when the dispersions are relatively constant.

The presence of $Li^+$ ions in serum solutions (prepared as described above) has been quantitatively determined by running the reflectance spectra of the colored areas of the plastic film. The FIGURE demonstrates that while the dye-peak (615 nm) appeared for all the lithium-containing samples, the same peak is distinctly absent in a lithium-free sample. Changes in reflectances of such samples are presented in $-\text{Log}(R)$ Scale ($R=$reflectivity), which is roughly equivalent to the absorbancy as measured by the widely known integrated sphere technique. The FIGURE also demonstrates that the reflectances of the samples vary as a function of concentration of lithium.

What is claimed is:

1. An analytical kit for selectively determining the lithium content of a sample comprising:
    (a) lithium selective color indicator comprising a leuco precursor of an arylmethane dye dispersed in a matrix, with all or a portion of said indicator being capable of reacting with lithium to develop a color when contacted with a sample containing lithium, and
    (b) means for measuring any color development of all or a portion of said indicator after it has been contacted with a sample and indicating the lithium content of such a sample based on any such color development.

2. The analytical kit of claim 1 wherein said measuring and indicating means (b) is a light scanning source capable of detecting a change in reflectivity of all or a portion of said indicator after it has been in contact with a sample.

3. The analytical kit of claim 1 wherein said measuring and indicating means (b) is a predetermined color intensity chart depicting colors obtained after contacting of said indicators like that of (a) with various known concentrations of lithium; whereby all or a portion of said indicator that has been contacted with a sample can be compared with the colors on said chart to indicate the lithium content of such a sample.

4. The analytical kit of claim 3 wherein said lithium ion selective indicator is coated on a substrate that provides a white background for a visual determination of any development of color corresponding to a lithium content of less than about 3 meq/L in a sample.

5. A method for selectively detecting the presence lithium in a sample comprising the steps of:
   (a) contacting all or a portion of a leuco precursor of an arylmethane dye with a sample to develop a color when the sample contains lithium, and
   (b) monitoring any development of color as an indication of the presence of lithium in the sample.

6. The method of claim 5 wherein said monitoring step (b) is a visual observation of color.

7. The method of claim 5 further comprising step (c) comparing any development of color to a color corresponding to a known concentration of lithium to determine the concentration of lithium in the sample.

8. The method of claim 7 wherein said sample comprises blood serum having potassium ions in excess of about 10 mM and sodium ions in excess of about 145 mM.

9. The method of claim 5 wherein said monitoring step (b) is accomplished by subjecting said contacted portion of said leuco precursor to a scanning light source to detect a change in reflectivity from that of a leuco precursor that has not contacted lithium.

10. The method of claim 9 wherein said leuco precursor of an arylmethane dye is selected from the group consisting of triarylmethane dye precursors, diarylmethane dye precursors, and any combination thereof.

11. The method of claim 10 wherein said leuco precursor is selected from the group consisting of 4,4-bis-dimethylaminobenzhydrol or derivative thereof.

12. The method of claim 11 wherein said leuco precursor is coated on a substrate.

13. The method of claim 12 wherein said substrate is polyethylene coated with silicone.

* * * * *